United States Patent [19]
Singh

[11] Patent Number: 6,001,876
[45] Date of Patent: Dec. 14, 1999

[54] ISOBUTYLGABA AND ITS DERIVATIVES FOR THE TREATMENT OF PAIN

[75] Inventor: Lakhbir Singh, Cambridgeshire, United Kingdom

[73] Assignee: Warner-Lambert Company, Morris Plains, N.J.

[21] Appl. No.: 09/043,358

[22] PCT Filed: Jul. 16, 1997

[86] PCT No.: PCT/US97/12390

§ 371 Date: Jul. 15, 1998

§ 102(e) Date: Jul. 15, 1998

[87] PCT Pub. No.: WO98/03167

PCT Pub. Date: Jan. 29, 1998

Related U.S. Application Data

[60] Provisional application No. 60/022,337, Jul. 24, 1996.

[51] Int. Cl.$^6$ .................................................. A61K 31/195
[52] U.S. Cl. .......................................................... 514/561
[58] Field of Search .............................................. 514/561

[56] References Cited

U.S. PATENT DOCUMENTS 5,563,175  10/1996  Silverman et al. ..................... 514/561

FOREIGN PATENT DOCUMENTS 9209560  6/1992  WIPO .
9323383  11/1993  WIPO .

*Primary Examiner*—James H. Reamer
*Attorney, Agent, or Firm*—Elizabeth M. Anderson

[57] ABSTRACT

The instant invention is a method of using certain analogs of glutamic acid and gamma-aminobutyric acid in pain therapy.

15 Claims, 18 Drawing Sheets

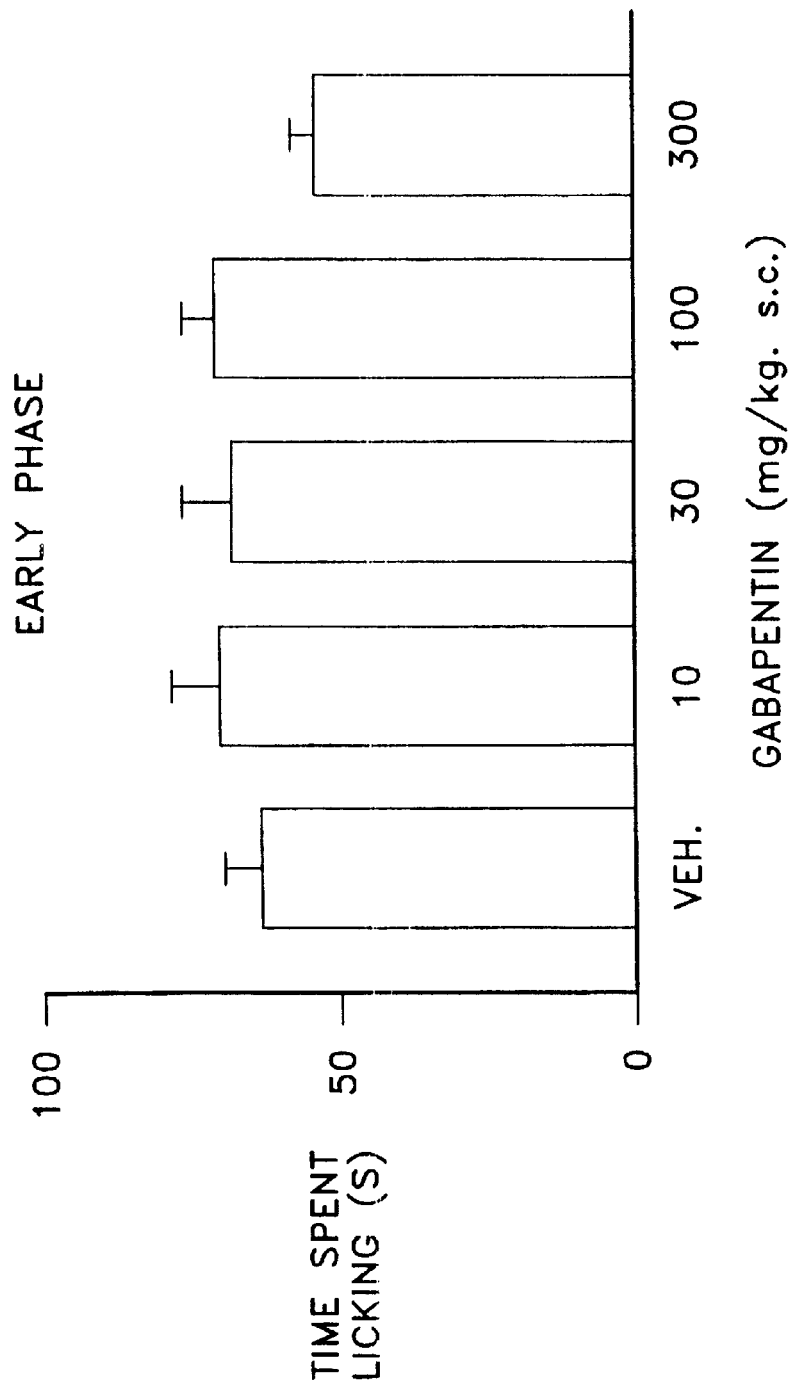
FIG-1a GABAPENTIN

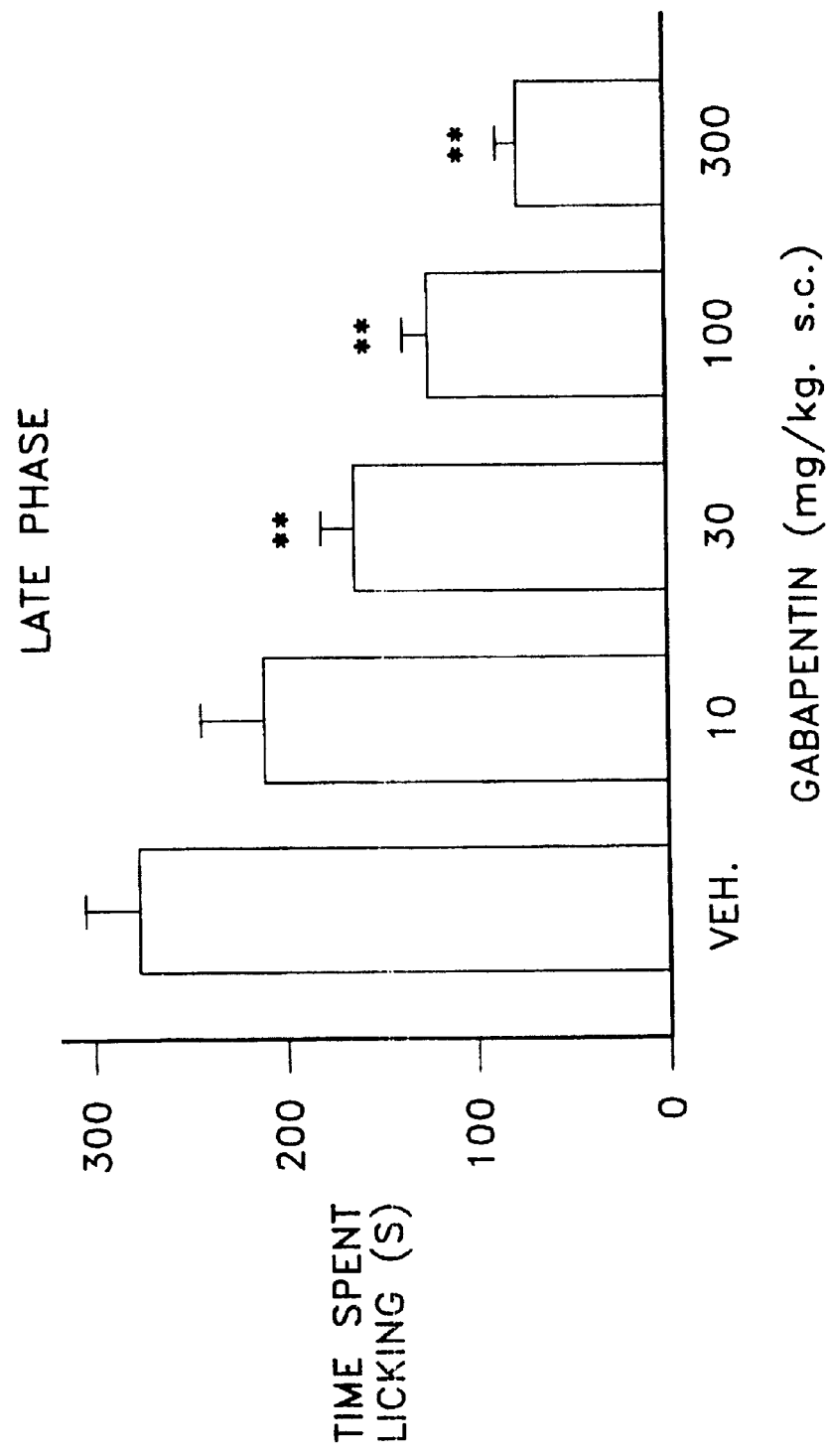
FIG-1b GABAPENTIN

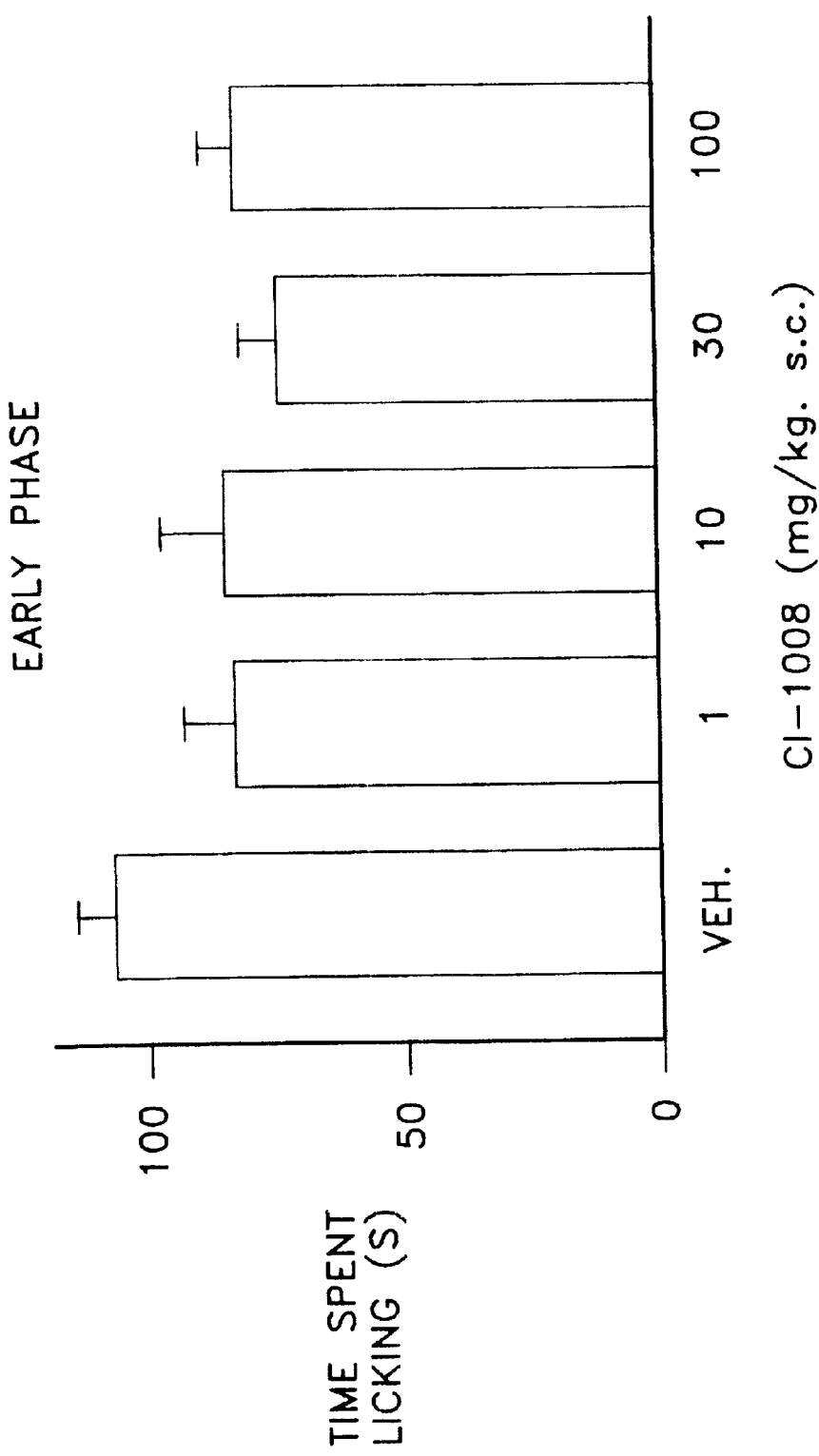
FIG-1c CI-1008

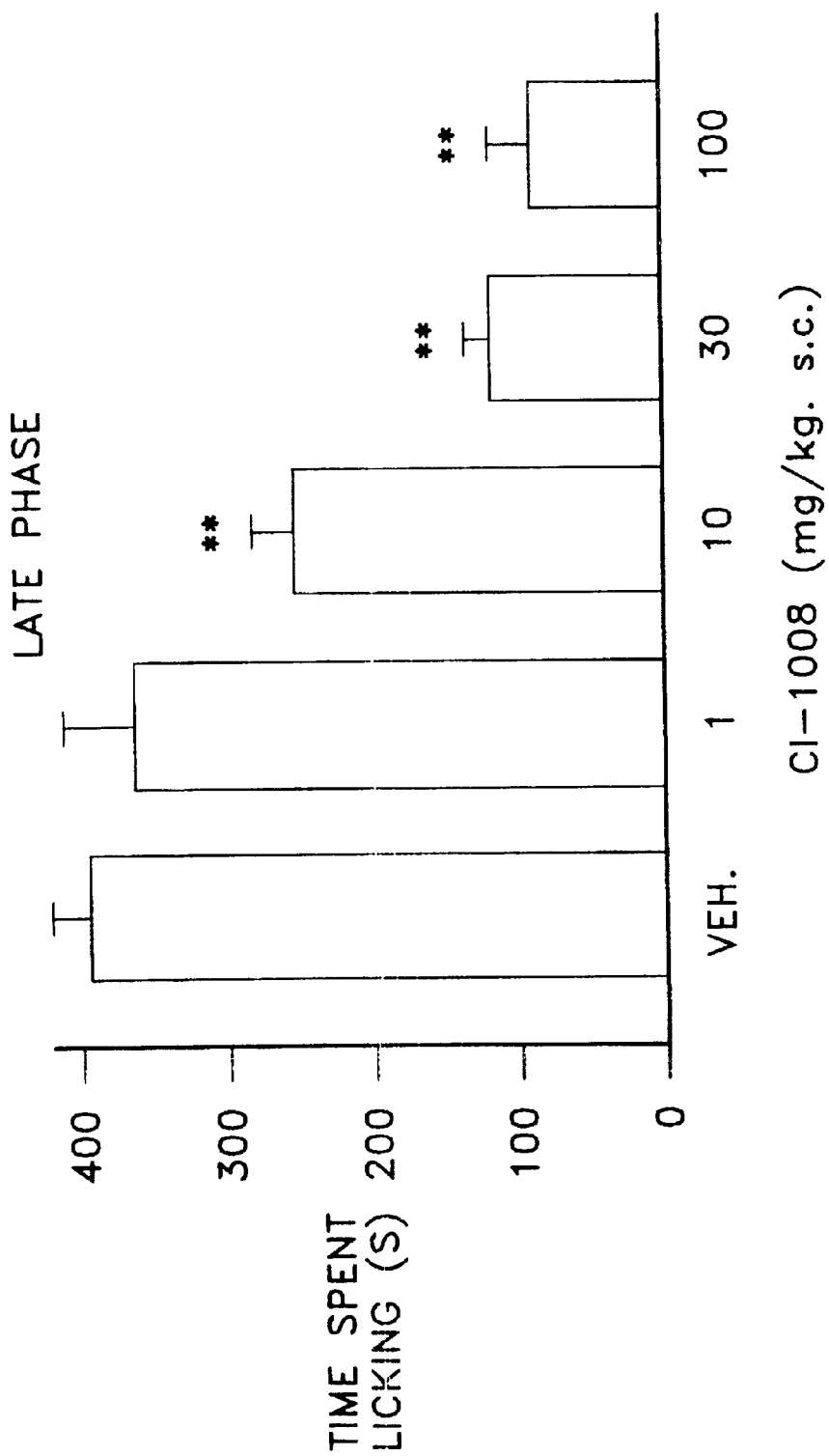
FIG-1d CI-1008

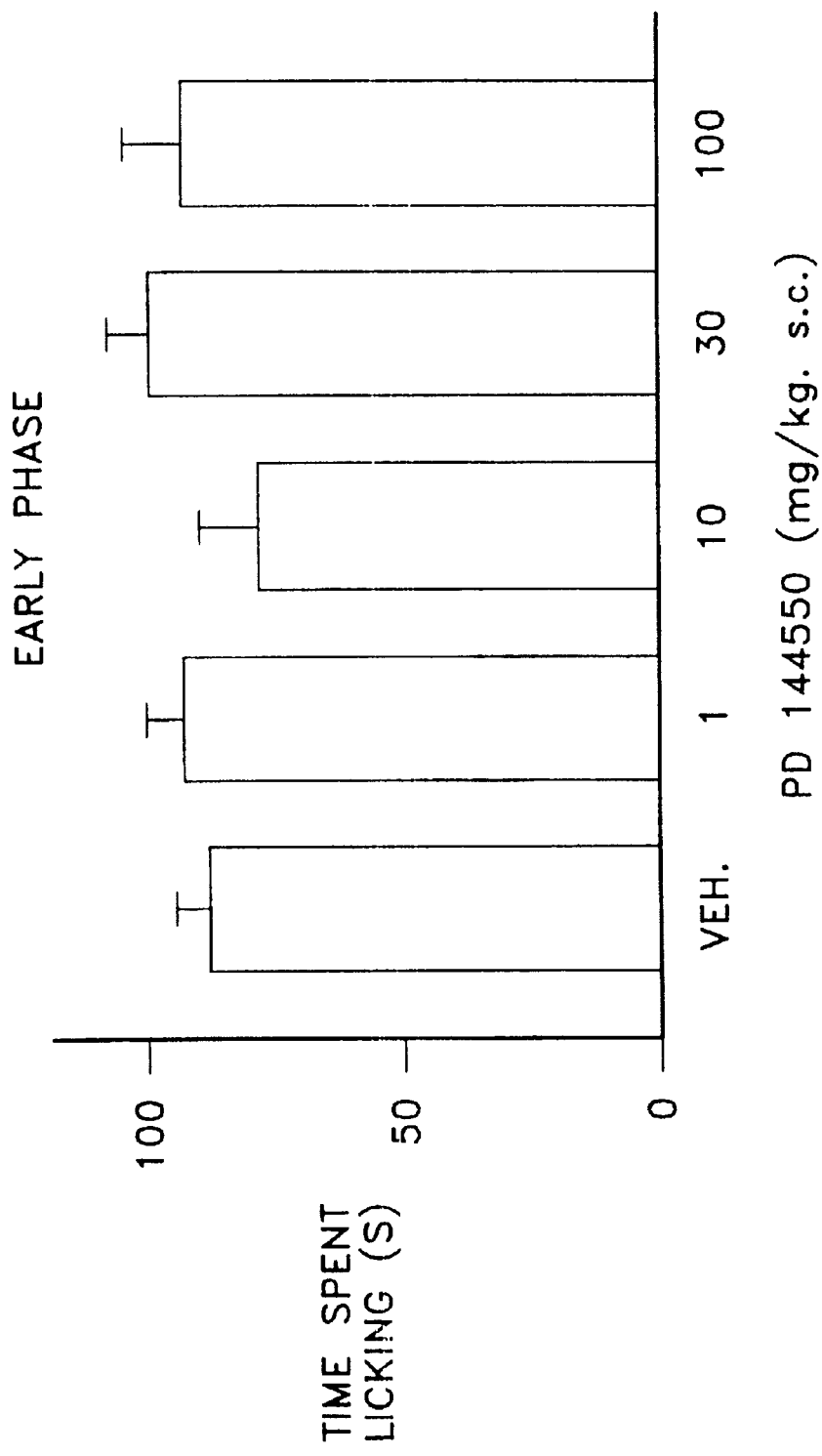
FIG-1e PD 144550

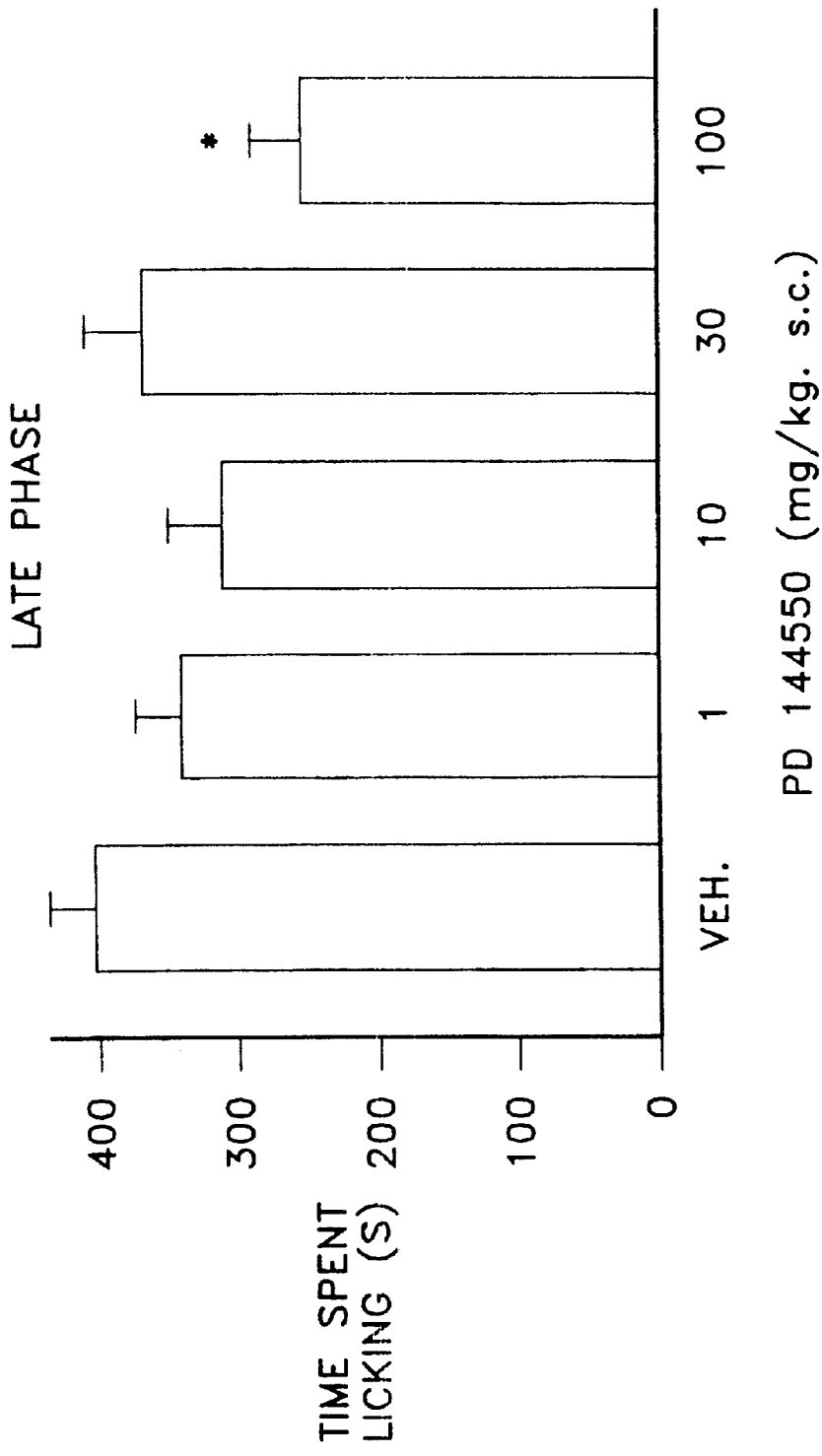
FIG-1f PD 144550

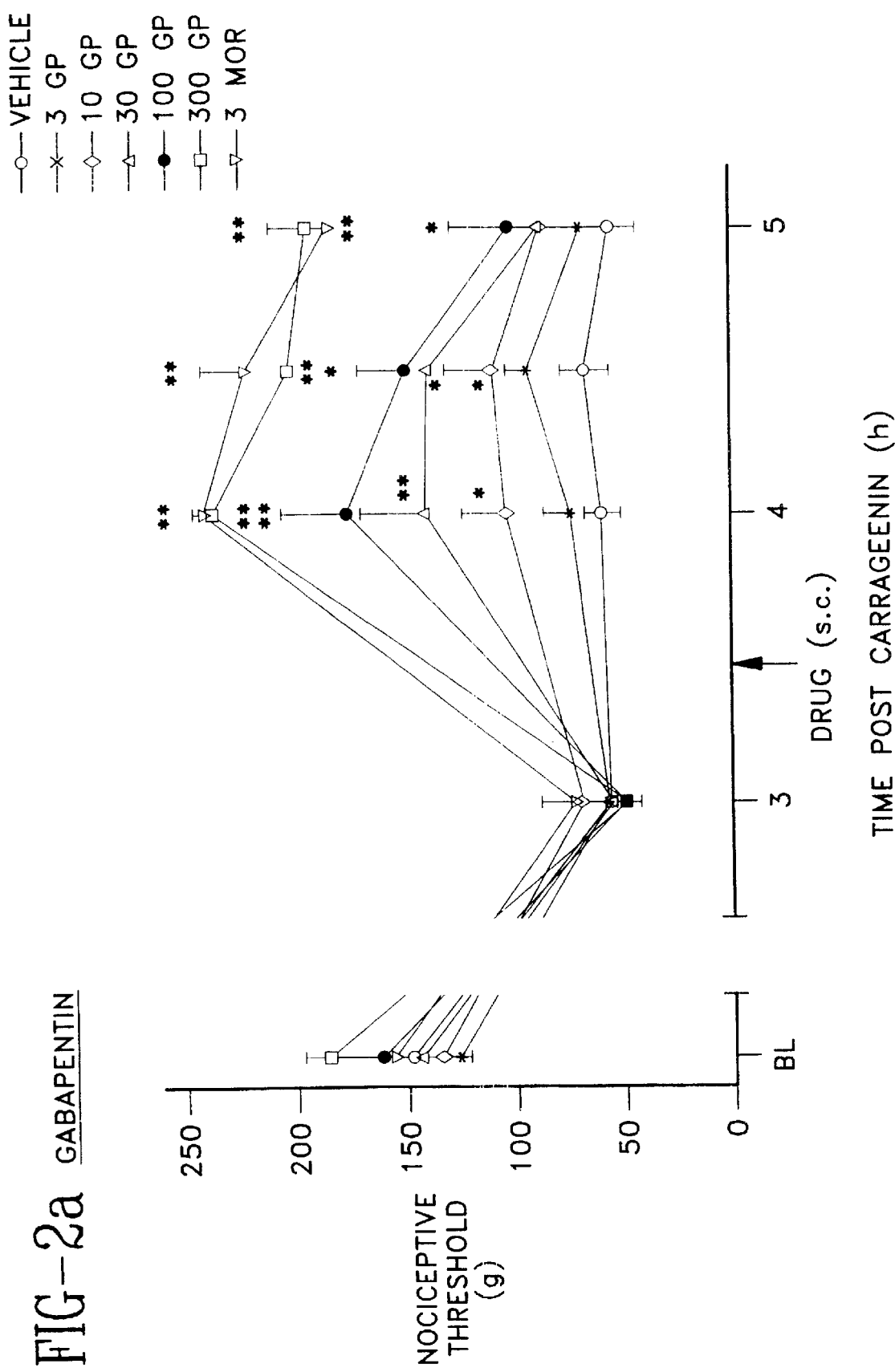

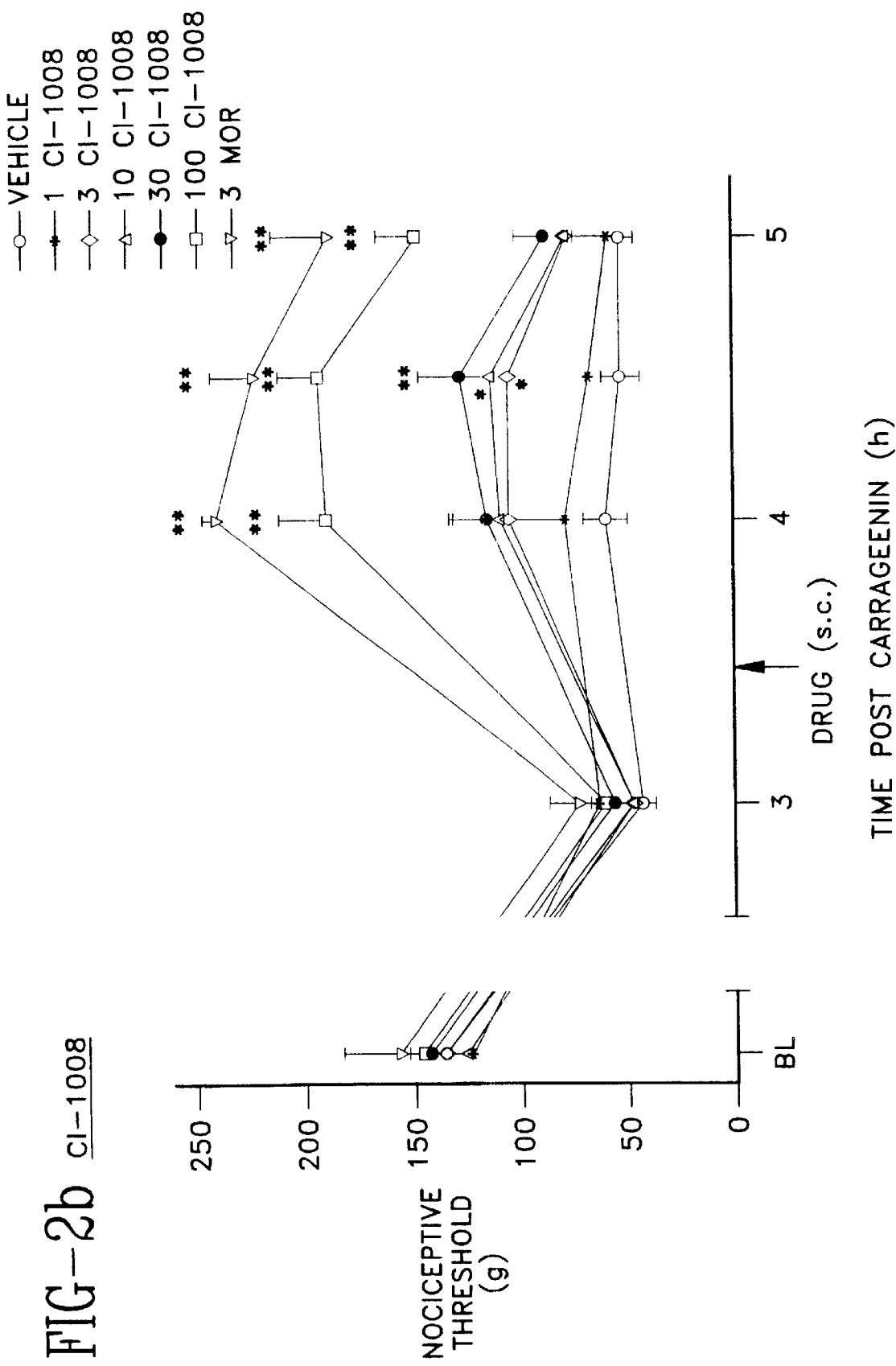
FIG-2b CI-1008

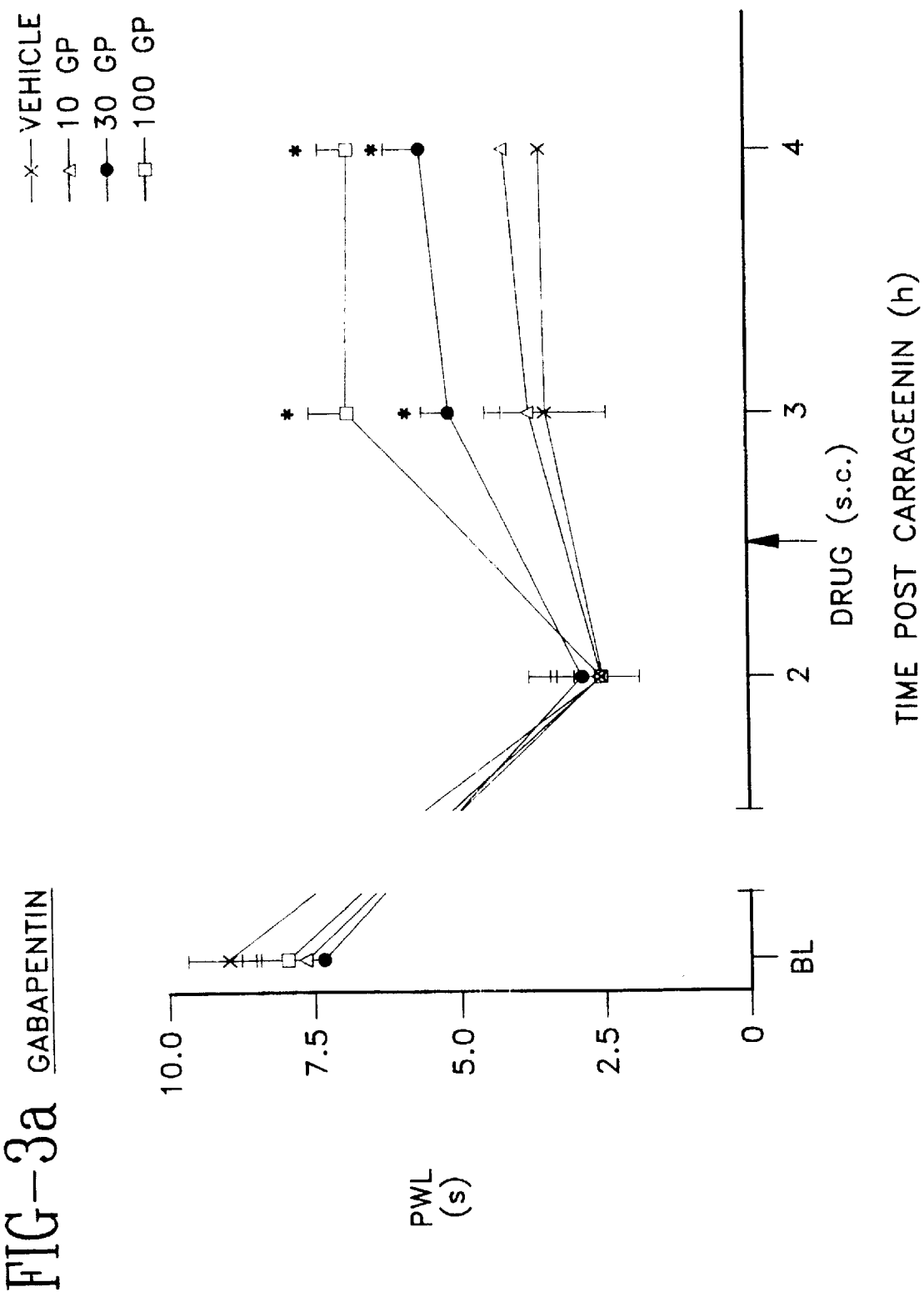
FIG-3a GABAPENTIN

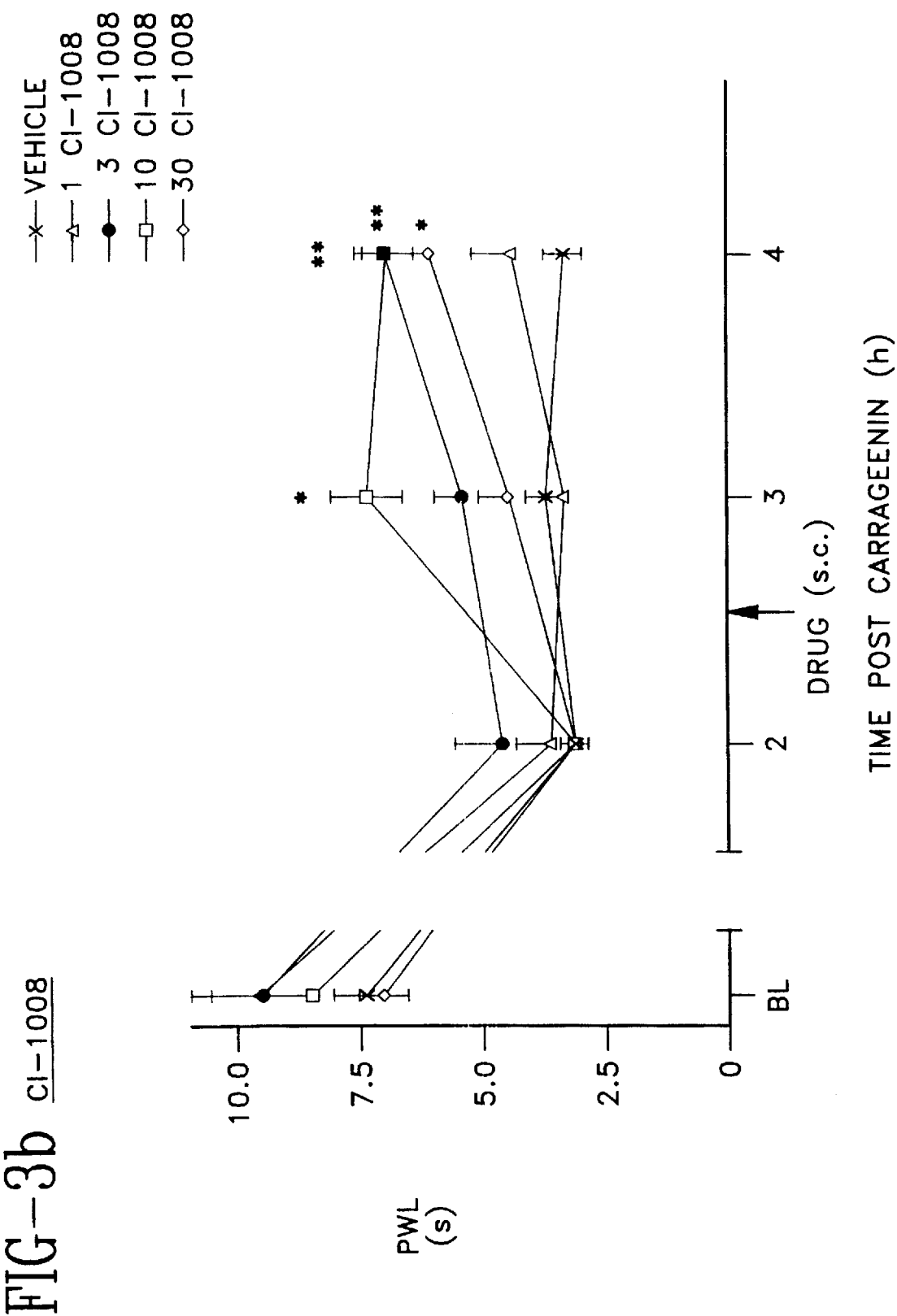
FIG-3b CI-1008

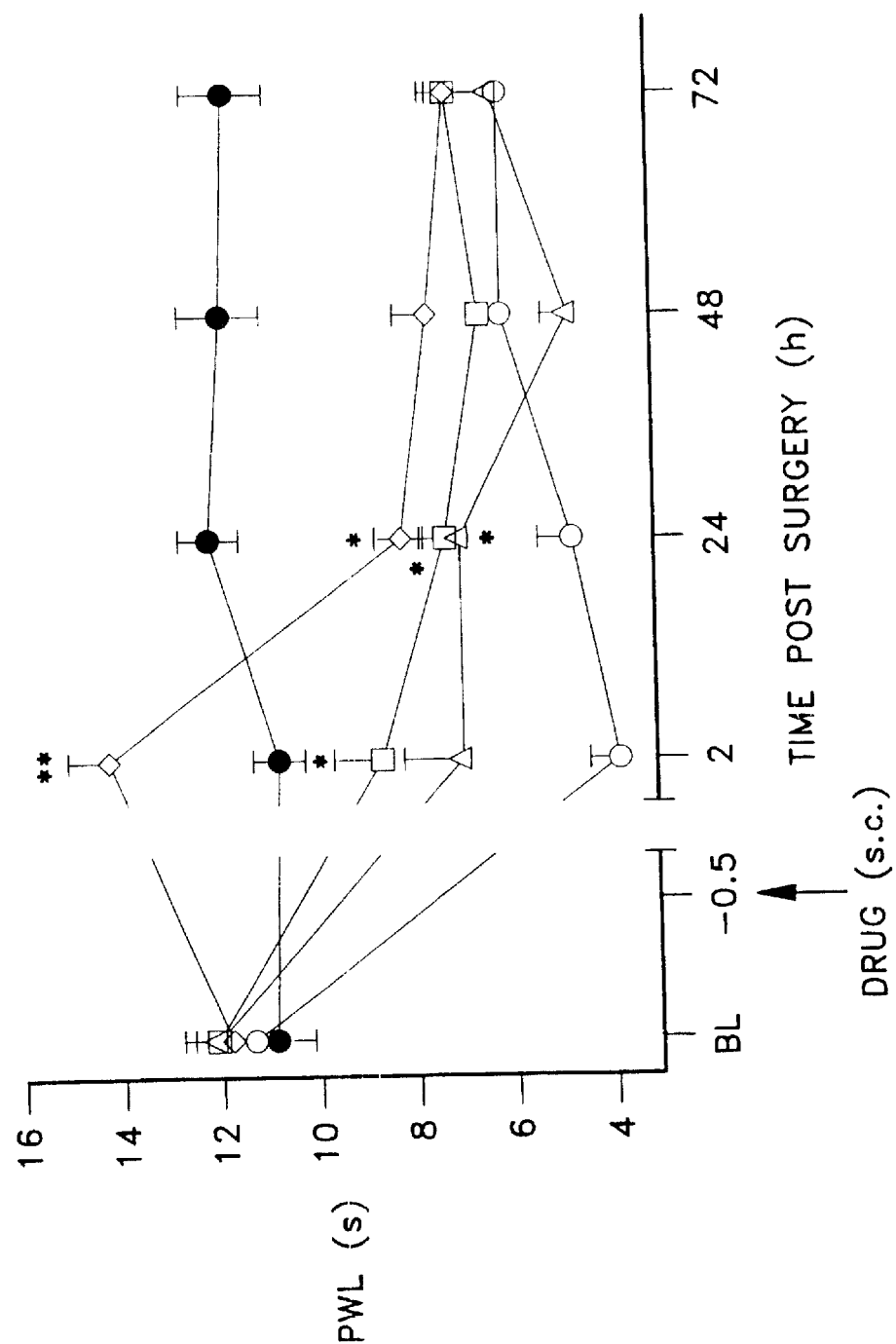

ISOBUTYLGABA AND ITS DERIVATIVES FOR THE TREATMENT OF PAIN

This application claims benefit of Provisional application Ser. No. 60/022,337, Jul. 24, 1996.

BACKGROUND OF THE INVENTION

The present invention is the use of analogs of glutamic acid and gamma-aminobutyric acid (GABA) in pain therapy, as the compounds exhibit analgesic/antihyperalgesic action. Advantages of the use of the compounds includes the finding that repeated use does not lead to tolerance nor is there a cross-tolerance between morphine and the compounds.

The compounds of the invention are known agents useful in antiseizure therapy for central nervous system disorders such as epilepsy, Huntington's chorea, cerebral ischemia, Parkinson's disease, tardive dyskinesia, and spasticity. It has also been suggested that the compounds can be used as antidepressants, anxiolytics, and antipsychotics. See WO 92/09560 (U.S. Ser. No. 618,692 filed Nov. 27, 1990) and WP 93/23383 (U.S. Ser. No. 886,080 filed May 20, 1992).

SUMMARY OF THE INVENTION

The instant invention is a method of using a compound of Formula I below in the treatment of pain, especially for treatment of chronic pain disorders. Such disorders include, but are not limited to, inflammatory pain, postoperative pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, bum pain, and other forms of neuralgic, neuropathic, and idiopathic pain syndromes.

A compound are those of Formula I

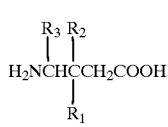

I or a pharmaceutically acceptable salt thereof wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl.

Diastereomers and enantiomers of compounds of Formula I are included in the invention.

Preferred compounds of the invention are those according to claim 1 wherein $R_3$ and $R_2$ are hydrogen, and $R_1$ is —$(CH_2)_{0-2}$—i $C_4H_9$ as an (R), (S), or (R,S) isomer.

The more preferred compounds of the invention are (S)-3-(aminomethyl)-5-methylhexanoic acid and 3-aminomethyl-5-methyl-hexanoic acid.

BRIEF DESCRIPTION OF THE DRAWINGS

FIG. 1. Effect of Gabapentin (1-(aminomethyl)-cyclohexaneacetic acid), CI-1008 ((S)-3-(aminomethyl)-5-methylhexanoic acid), and 3-aminomethyl-5-methyl-hexanoic acid in the Rat Paw Formalin Test Test compounds were administered s.c. 1 hour before an intraplantar injection of 50 µL formalin. The time spent licking/biting the injected paw during the early and late phases was scored. Results are shown as the mean ±SEM of 6 to 8 animals per group. *P<0.05 and **P<0.01 significantly different from vehicle (Veh.) treated controls (ANOVA followed by Dunnett's t-test).

FIG. 2. Effect of Gabapentin and CI-1008 on Carrageenin-Induced Mechanical Hyperalgesia Nociceptive pressure thresholds were measured in the rat using the paw pressure test. Baseline (BL) measurements were taken before animals were administered with 100 µL of 2% carrageenin by intraplantar injection. Results are shown as mean (±SEM) of 8 animals per group. Gabapentin (GP), CI-1008, or morphine (MOR; 3 mg/g) was administered s.c. 3.5 hours after carrageenin. *P<0.05 and **P<0.01 significantly different from vehicle control group at the same time point (ANOVA followed by Dunnett's t-test).

FIG. 3. Effect of Gabapentin and CI-1008 on Carrageenin-Induced Thermal Hyperalgesia Nociceptive thermal thresholds were measured in the rat using the Hargreaves apparatus. Baseline (BL) measurements were taken before animal s were administered with 100 µL of 2% carrageenin by intraplantar injection. Results are shown as mean (±SEM) of 8 animals per group. Gabapentin (GP) or CI-1008 was administered s.c. 2.5 hours after carrageenin. *P<0.05 and **P<0.01 significantly different from vehicle control group at the same time point (ANOVA followed by Dunnett's t-test).

In FIG. 5, —●— is vehicle contralateral, —○— is vehicle ispsilateral. For morphine (5a), —△— is 1 mg/kg, —□— is 3, and —◇— is 16.

In 5b for gabapentin and S-(+)-isobutylgaba, —△— is 3 mg/kg, —□— is 10, and —◇— is 30.

Figure 4B:
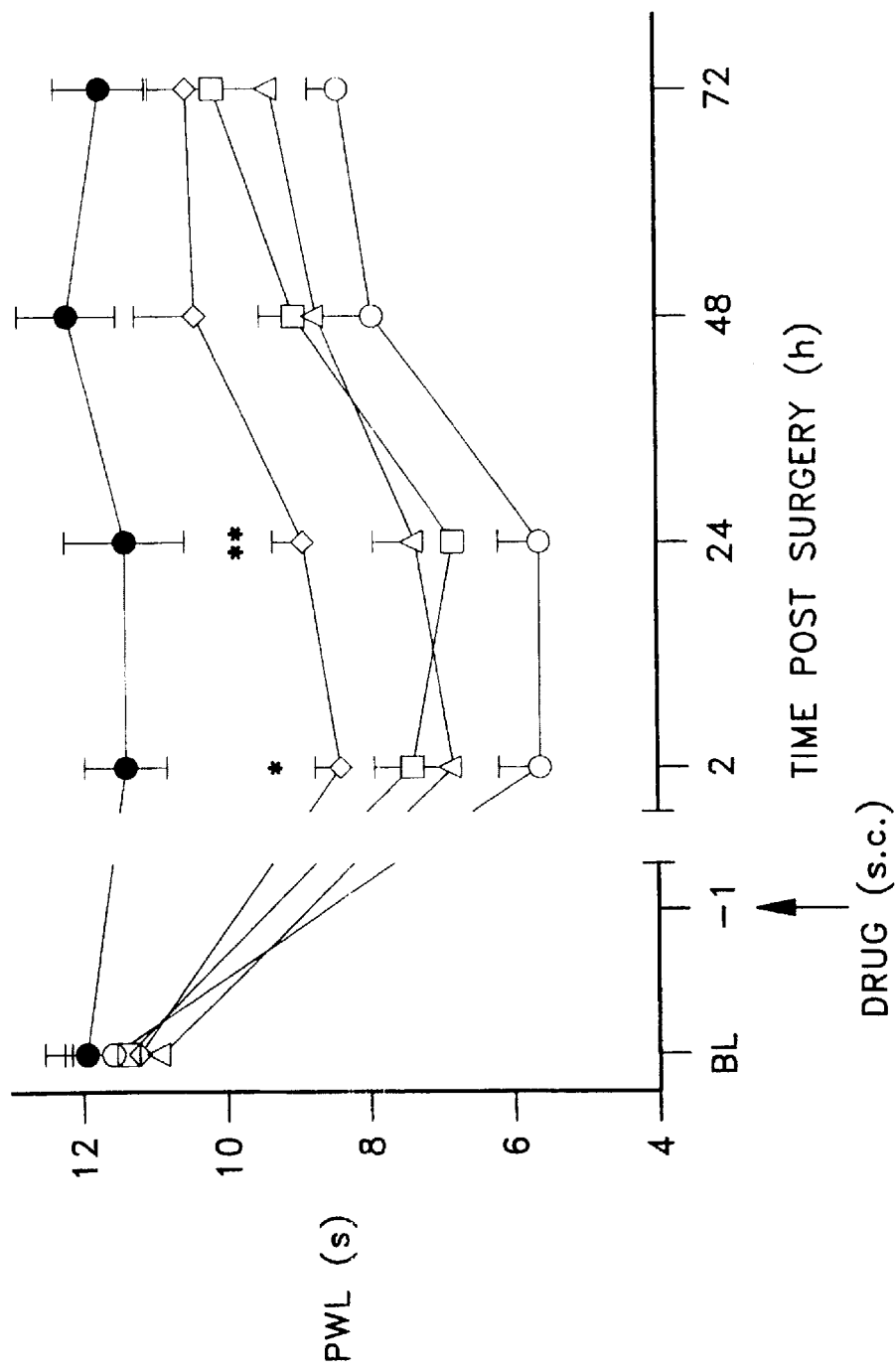
FIG. 4. Effect of (a) Morphine, (b) Gabapentin, and (c) S-(+)-3-Isobutylgaba on Thermal Hyperalgesia in the Rat Postoperative Pain Model Gabapentin or S-(+)-3 isobutylgaba was administered 1 hour before surgery. Morphine was administered 0.5 hour before surgery. Thermal paw withdrawal latencies (PWL) were determined for both ipsilateral and contralateral paws using the rat plantar test. For clarity contralateral paw data for drug-treated animals is not shown. Baseline (BL) measurements were taken before surgery and PWL were reassessed 2, 24, 48, and 72 hours postsurgery. Results are expressed as the mean PWL(s) of 8 to 10 animals per group (vertical bars represent ±SEM). *P<0.05 **P<0.01 significantly different (ANOVA followed by Dunnett's t-test), comparing ipsilateral paw of drug-treated groups to ispsilateral paw of vehicle-treated group at each time point. In the figure, —●— is vehicle contralateral, —○— is vehicle ispsilateral, —△— is 1 mg/kg morphine, —□— is 3, and —◇— is 6 for morphine in 4a. In 4b, —△— is 3, —□— is 10, and —◇— is 30 for gabapentin. In 4c, —△— is 3 mg/kg, —□— is 10, and —◇— is 30 for S-(+)-isobutylgaba.
Figure 4C:
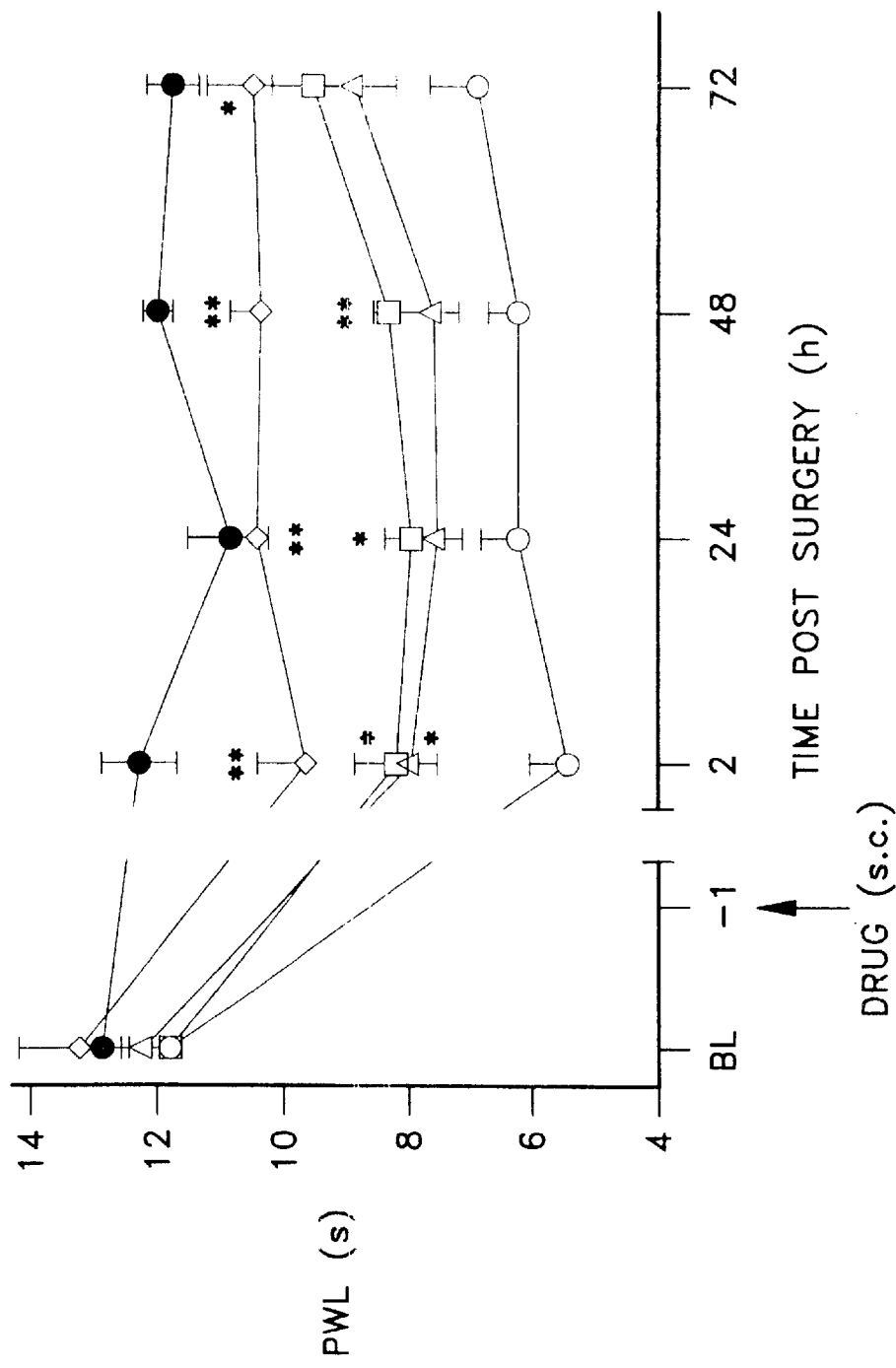
Figure 5A:
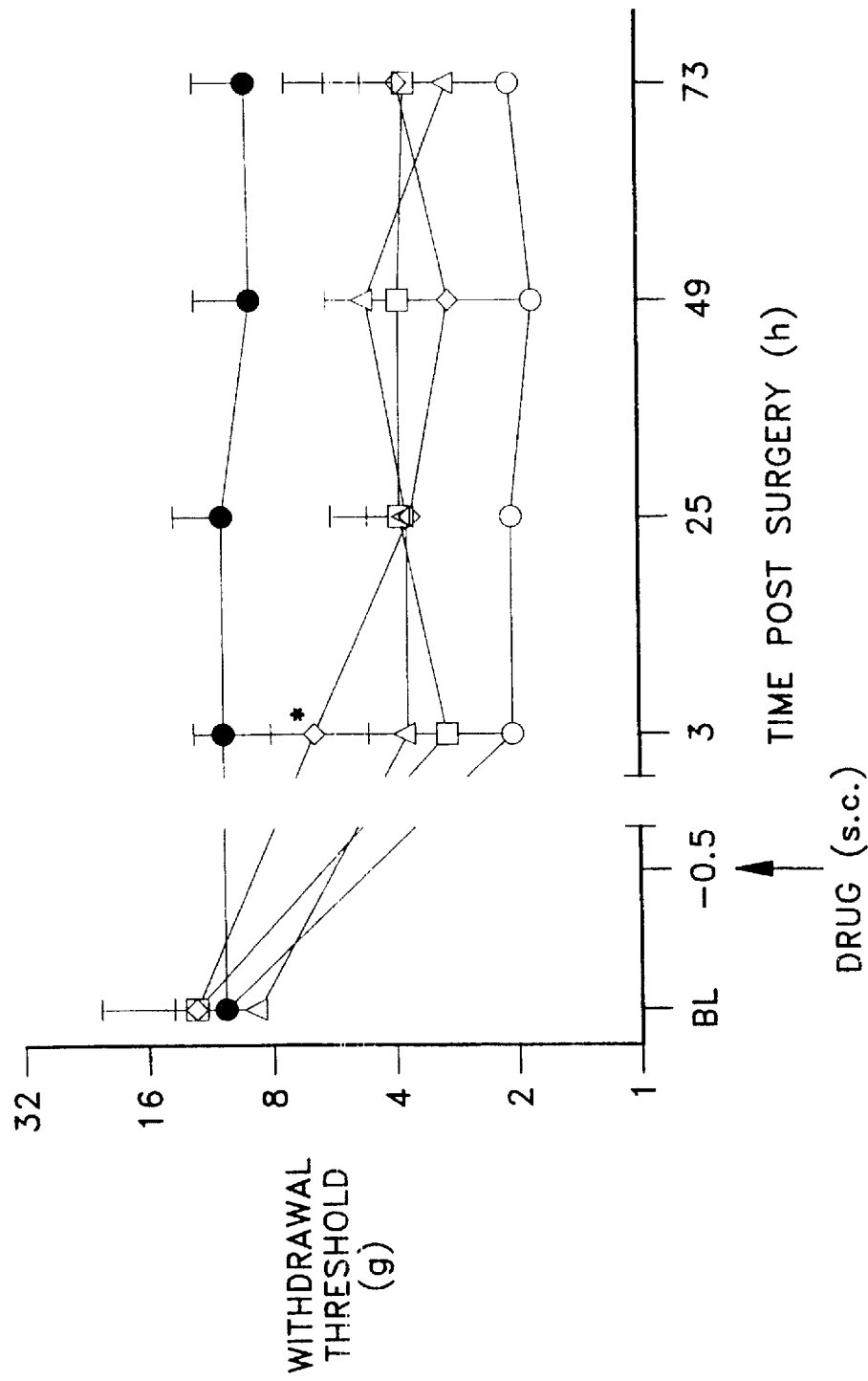
FIG. 5 Effect of (a) Morphine, (b) Gabapentin, and (c) S-(+)-3-Isobutylgaba on Tactile Allodynia in the Rat Postoperative Pain Model Gabapentin or S-(+)-3-isobutylgaba was administered 1 hour before surgery. Morphine was administered 0.5 hour before surgery. Paw withdrawal thresholds to von Frey hair filaments were determined for both ipsilateral and contralateral paws. For clarity, contralateral paw data for drug-treated animals is not shown. Baseline (BL) measurements were taken before surgery, and withdrawal thresholds were reassessed 3, 25, 49, and 73 hours postsurgery. Results are expressed as median force (g) required to induce a withdrawal of paw in 8 to 10 animals per group (vertical bars represent first and third quartiles). *P<0.05 significantly different (Mann Whitney t-test) comparing ipsilateral paw of drug-treated groups to ipsilateral paw of vehicle treated group at each time point.
Figure 5B:
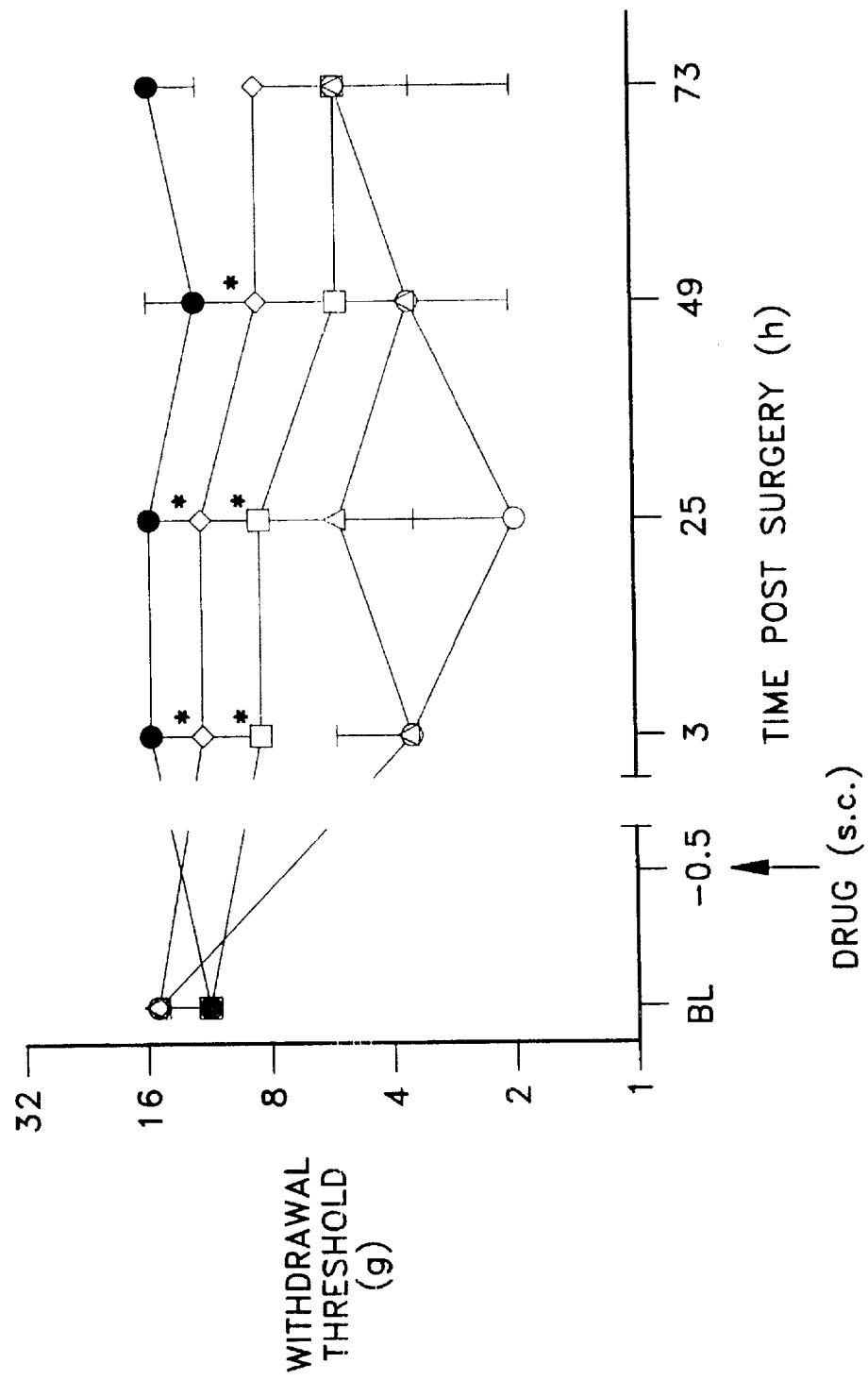
Figure 5C:
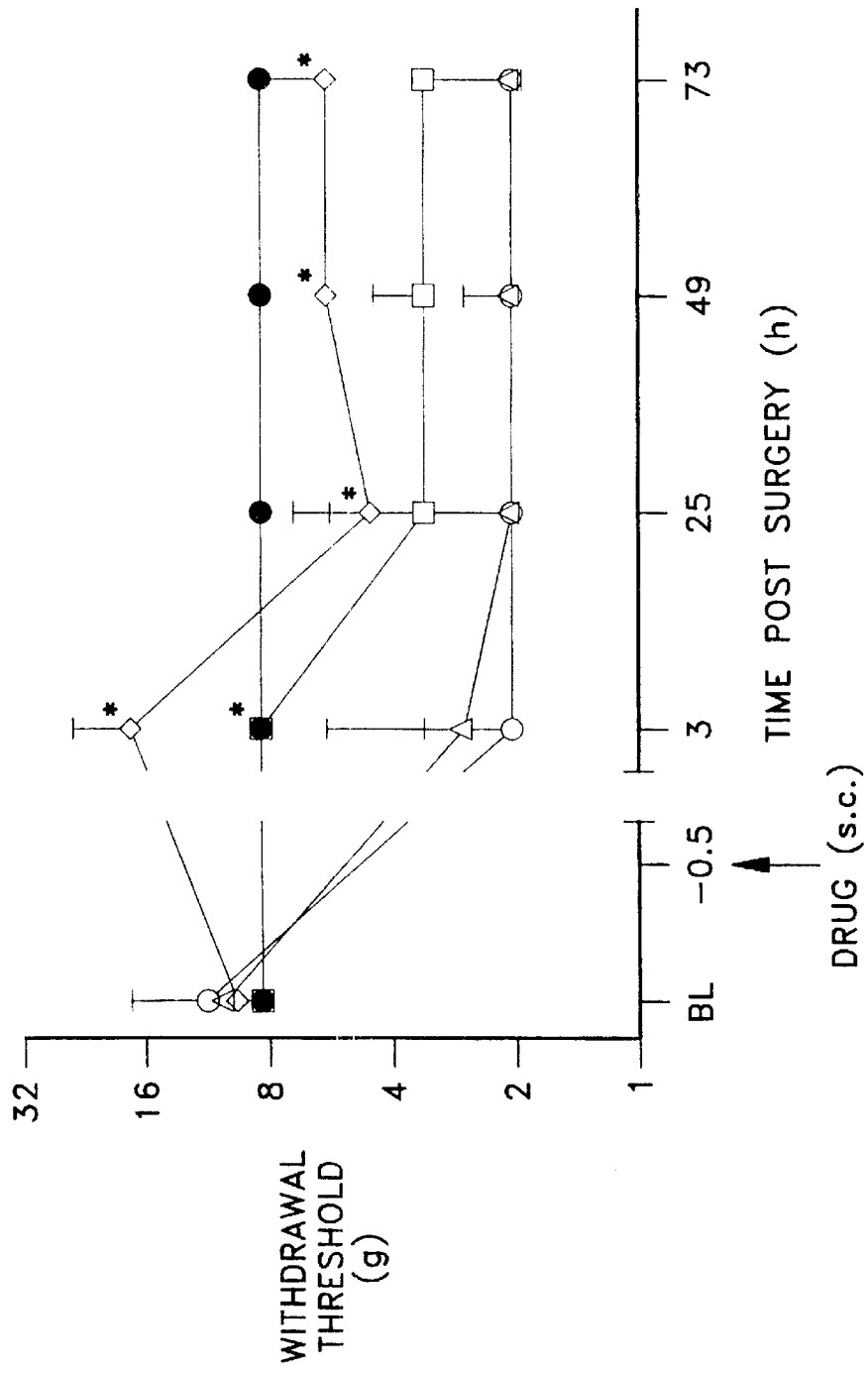
Figure 6A:
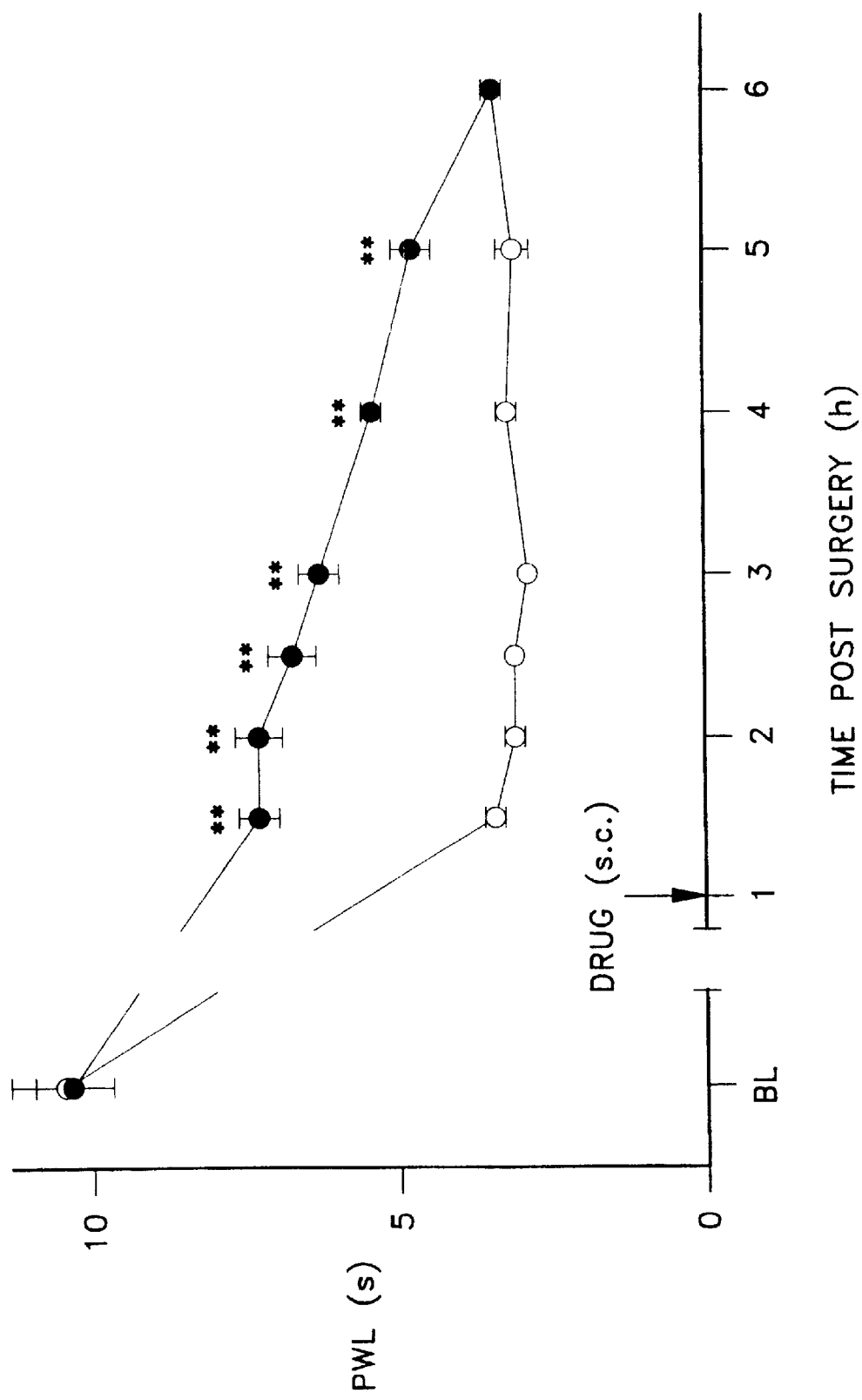
Figure 6B:
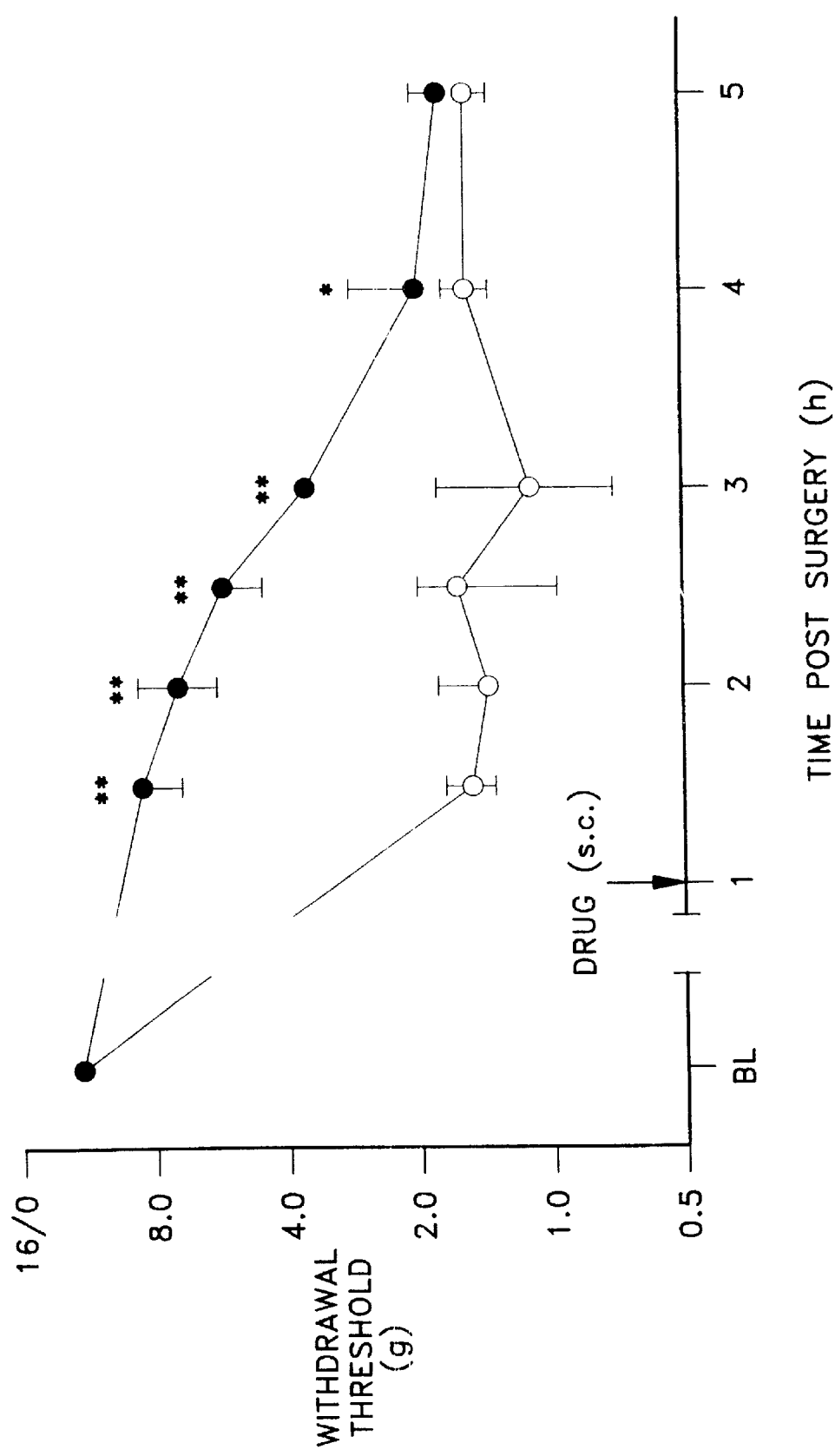

FIG. 6. Effect of S-(+)-3-Isobutylgaba on the Maintenance of (a) Thermal Hyperalgesia and (b) Tactile Allodynia in the Rat Postoperative Pain Model.

S-(+)-3-Isobutylgaba (S-(+)-IBG) was administered 1 hour after surgery. Thermal paw withdrawal latencies, determined using the rat plantar test, and paw withdrawal thresholds to von Frey hair filaments, were determined in separate groups of animals for both ipsilateral and contralateral paws. For clarity only the ipsilateral paw data is shown. Baseline (BL) measurements were taken before surgery and withdrawal thresholds were reassessed up to 6 hours postsurgery. For thermal hyperalgesia, the results are expressed as the mean PWL(s) of 6 animals per group (vertical bars represent ±SEM), *P<0.05 **P<0.01 significantly different (unpaired t-test), comparing ipsilateral paw of drug-treated group to ipsilateral paw of vehicle (Veh —○—) treated group at each time point. For tactile allodynia, the results are expressed as median force (g) required to induce a paw withdrawal of 6 animals per group (vertical bars represent first and third quartiles). *P<0.05 significantly different (Mann Whitney t-test), comparing ipsilateral paw of drug-treated group to ipsilateral paw of vehicle-treated group at each time point. —●— is S-(+)-IBG at 30 mg/kg.

DETAILED DESCRIPTION

The instant invention is a method of using a compound of Formula I above as an analgesic in the treatment of pain as listed above. Pain such as inflammatory pain, neuropathic pain, cancer pain, postoperative pain, and idiopathic pain which is pain of unknown origin, for example, phantom limb pain are included especially. Neuropathic pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

The conditions listed above are known to be poorly treated by currently marketed analgesics such as narcotics or nonsteroidal anti-inflammatory drugs (NSAID) due to insufficient efficacy or limiting side effects.

The terms used in Formula I are, for example, alkyl which term is methyl, ethyl, propyl, isopropyl, n-butyl, isobutyl, sec-butyl, tert-butyl, isopentyl, and neopentyl, as well as those as would occur to one skilled in the art.

The term "cycloalkyl" is exemplified by cyclopropyl, cyclobutyl, cyclopentyl, and cyclohexyl.

The compounds of the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts.

The compounds of the present invention can contain one or several asymmetric carbon atoms. The invention includes the individual diastereomers or enantiomers, and the mixtures thereof. The individual diastereomers or enantiomers may be prepared or isolated by methods already well-known in the art.

The method for the formation of the 3-alkyl-4-aminobutanoic acids starting from 2-alkenoic esters is prepared from commercially available aldehydes and monoethyl malonate by the Knoevenagel reaction (Kim Y. C., Cocolase G. H., *J. Med. Chem.,* 1965:8509), with the exception of ethyl 4,4-dimethyl-2-pentenoate. This compound was prepared from 2,2-dimethylpropanal and ethyl lithioacetate, followed by dehydration of the β-hydroxyester with phosphoryl chloride and pyridine. The Michael addition of nitromethane to α,β-unsaturated compounds mediated by 1,1,3,3-tetramethylguanidine or 1,8-diazabicyclo [5.4.0]undec-7-ene(DBU) afforded 4-nitroesters in good yields.

Although the aliphatic nitro compounds are usually reduced by either high pressure catalytic hydrogenation by metal-catalyzed transfer hydrogenation, or by newly introduced hydrogenolysis methods with ammonium formate or sodium borohydride and palladium as catalysts, applicants have found that 4-nitrocarboxylic esters can be reduced almost quantitatively to the corresponding 4-aminocarboxylic esters by hydrogenation using 10% palladium on carbon as catalysts in acetic acid at room temperature and atmospheric pressure. The amino esters produced were subjected to acid hydrolysis to afford the subject inventive compounds in good yields. This procedure provides access to a variety of 3-alkyl-4-aminobutanoic acids as listed in Tables 1 and 2 as examples, and thus is advantageous in comparison to methods previously used.

When the starting material is not commercially available, the synthetic sequence was initiated with the corresponding alcohol, which was oxidized to the aldehyde by the method of Corey, et al., *Tetrahedrom. Lett.,* 1975:2647–2650.

The compounds made by the synthetic methods can be used as pharmaceutical compositions as agent in the treatment of pain when an effective amount of a compound of the Formula I, together with a pharmaceutically acceptable carrier is used. The pharmaceutical can be used in a method for treating such disorders in mammals, including human, suffering therefrom by administering to such mammals an effective amount of the compound as described above in unit dosage form.

The pharmaceutical compound, made in accordance with the present invention, can be prepared and administered in a wide variety of dosage forms by either oral or parenteral routes of administration. For example, these pharmaceutical compositions can be made in inert, pharmaceutically acceptable carriers which are either solid or liquid. Solid form preparations include powders, tablets, dispersible granules, capsules, cachets, and suppositories. Other solid and liquid form preparations could be made in accordance with known methods of the art and administered by the oral route in an appropriate formulation, or by a parenteral route such as intravenous, intramuscular, or subcutaneous injection as a liquid formulation.

The quantity of active compound in a unit dose of preparation may be varied or adjusted from 1 mg to about 300 mg/kg daily, based on an average 70-kg patient. A daily dose range of about 1 mg to about 50 mg/kg is preferred. The dosages, however, may be varied depending upon the requirement with a patient, the severity of the condition being treated, and the compound being employed. Determination of the proper dosage for particular situations is within the skill of the art.

Effects of Gabapentin, CI-1008, and 3-Aminomethyl-5-methyl-hexanoic Acid in the Rat Formalin Paw Test Male Sprague-Dawley rats (70–90 g) were habituated to perspex observation chambers (24 cm×24 cm×24 cm) for at least 15 minutes prior to testing. Formalin-induced hind paw licking and biting was initiated by a 50 µL subcutaneous injection of a 5% formalin solution (5% formaldehyde in isotonic saline) into the plantar surface of the left hind paw. Immediately following the formalin injection, licking/biting of the injected hind paw was scored in 5 minute bins for 60 minutes. The results are expressed as mean combined licking/biting time for the early phase (0–10 minutes) and late phase (10–45 minutes).

The s.c. administration of gabapentin (10–300 mg/kg) or CI-1008 (1–100 mg/kg) 1 hour before formalin dose-dependently blocked the licking/biting behavior during the late phase of the formalin response with respective minimum effective doses (MED) of 30 and 10 mg/kg (FIG. 1). However, neither of the compounds affected the early phase at any of the doses tested. Similar administration of 3-aminomethyl-5-methyl-hexanoic acid produced only a modest blockade of the late phase at 100 mg/kg.

Effects of Gabapentin and CI-1008 on Carrageenin-Induced Hyperalgesia

On the test Day, 2 to 3 baseline measurements were taken before rats (male Sprague-Dawley 70–90 g) were administered with 100 µL of 2% carrageenin by intraplantar injection into the right hind paw. Animals were dosed with the test drug after development of peak hyperalgesia. Separate groups of animals were used for the mechanical and thermal hyperalgesia studies.

A. Mechanical Hyperalgesia

Nociceptive pressure thresholds were measured in the rat paw pressure test using an analgesimeter (Ugo Basile). A cut-off point of 250 g was used to prevent any damage to the paw. The intraplantar injection of carrageenin produced a reduction in the nociceptive pressure threshold between 3 and 5 hours after injection, indicating induction of hyperalgesia. Morphine (3 mg/kg, s.c.) produced a complete blockade of hyperalgesia (FIG. 2). Gabapentin (3–300 mg/kg, s.c.) and CI-1008 (1–100 mg/kg, s.c.) dose-dependently antagonized the hyperalgesia, with respective MED of 10 and 3 mg/kg (FIG. 2).

B. Thermal Hyperalgesia

Baseline paw withdrawal latencies (PWL) were obtained for each rat using the Hargreaves model. Carrageenin was injected as described above. Animals were then tested for thermal hyperalgesia at 2 hours postcarrageenin administration. Gabapentin (10–100 mg/kg) or CI-1008 (1–30 mg/kg) was administered s.c. 2.5 hours after carrageenin, and PWL were reevaluated at 3 and 4 hours postcarrageenin administration. Carrageenin induced a significant reduction in paw withdrawal latency at 2, 3, and 4 hours following injection, indicating the induction of thermal hyperalgesia (FIG. 3). Gabapentin and CI-1008 dose-dependently antagonized the hyperalgesia with a MED of 30 and 3 mg/kg (FIG. 3).

These data show that gabapentin and CI-1008 are effective in the treatment of inflammatory pain.

The assay of Bennett G. J. provides an animal model of a peripheral mononeuropathy in rat that produces disorder of pain sensation like those seen in man (*Pain*, 1988;33:87–107).

The assay of Kim S. H., et al., provides one experimental model for peripheral neuropathy produced by segmented spinal nerve ligation in the rat (*Pain*, 1990;50:355–363).

A rat model of postoperative pain has been described (Brennan et al., 1996). It involves an incision of the skin, fascia, and muscle of the plantar aspect of the hind paw. This leads to an induction of reproducible and quantifiable mechanical hyperalgesia lasting several days. It has been suggested that this model displays some similarities to the human postoperative pain state. In the present study we have examined and compared the activities of gabapentin and S-(+)-3-isobutylgaba with morphine in this model of postoperative pain.

METHODS

Male Sprague-Dawley rats (250–300 g), obtained from Bantin and Kingmen, (Hull, U. K.) were used in all experiments. Before surgery, animals were housed in groups of 6 under a 12-hour light/dark cycle (lights on at 07 hour 00 minute) with food and water ad libitum. Postoperatively, animals were housed in pairs on "Aqua-sorb" bedding consisting of air laid cellulose (Beta Medical and Scientific, Sale, U.K.) under the same conditions. All experiments were carried out by an observer blind to drug treatments.

Surgery

Animals were anaesthetized with 2% isofluorane and 1.4 $O_2/NO_2$ mixture which was maintained during surgery via a nose cone. The plantar surface of the right hind paw was prepared with 50% ethanol, and a 1-cm longitudinal incision was made through skin and fascia, starting 0.5 cm from the edge of the heel and extending towards the toes. The plantaris muscle was elevated using forceps and incised longitudinally. The wound was closed using two simple sutures of braided silk with a FST-02 needle. The wound site was covered with Terramycin spray and Auromycin powder. Postoperatively, none of the animals displayed any signs of infection with the wounds healing well after 24 hours. The sutures were removed after 48 hours.

Evaluation of Thermal Hyperalgesia

Thermal hyperalgesia was assessed using the rat plantar test (Ugo Basile, Italy) following a modified method of Hargreaves, et al., 1988. Rats were habituated to the apparatus which consisted of three individual perspex boxes on an elevated glass table. A mobile radiant heat source was located under the table and focused onto the hind paw and paw withdrawal latencies (PWL) were recorded. There was an automatic cut off point of 22.5 seconds to prevent tissue damage. PWLs were taken 2 to 3 times for both hind paws of each animal, the mean of which represented baselines for right and left hind paws. The apparatus was calibrated to give a PWL of approximately 10 seconds. PWL(s) were reassessed following the same protocol as above 2, 24, 48, and 72 hours postoperatively.

Evaluation of Tactile Allodynia

Tactile allodynia was measured using Semmes-Weinstein von Frey hairs (Stoelting, Ill., U.S.A.). Animals were placed into wire-mesh-bottom cages allowing access to the underside of their paws. The animals were habituated to this environment prior to the start of the experiment. Tactile allodynia was tested by touching the plantar surface of the animals hind paw with von Frey hairs in ascending order of force (0.7, 1.2, 1.5, 2, 3.6, 5.5, 8.5, 11.8, 15. 1, and 29 g) until a paw withdrawal response was elicited. Each von Frey hair was applied to the paw for 6 seconds, or until a response occurred. Once a withdrawal response was established, the paw was retested, starting with the next descending von Frey hair until no response occurred. The highest force of 29 g lifted the paw as well as eliciting a response, thus represented the cut-off point. Each animal had both hind paws tested in this manner. The lowest amount of force required to elicit a response was recorded as withdrawal threshold in grams. When compounds were administered before surgery, the same animals were used to study drug effects on tactile, allodynia, and thermal hyperalgasia, with each animal being tested for tactile allodynia 1 hour after thermal hyperalgesia. Separate groups of animals were used for examination of tactile allodynia and thermal hyperalgesia when S-(+)-3-isobutylgaba was administered after surgery.

Statistics

Data obtained for thermal hyperalgesia was subjected to a one-way (analysis of variance) ANOVA followed by a Dunnett's t-test. Tactile allodynia results obtained with the von Frey hairs were subjected to an individual Mann Whitney t-test.

RESULTS

An incision of the rat plantaris muscle led to an induction of thermal hyperalgesia and tactile allodynia. Both nociceptive responses peaked within 1 hour following surgery and were maintained for 3 days. During the experimental period, all animals remained in good health.

Effect of Gabapentin. S-(+)-3-Isobutylgaba and Morphine Administered Before Surgery on Thermal Hyperalgesia The single-dose administration of gabapentin 1 hour before surgery dose-dependently (3–30 mg/kg, s.c.) blocked development of thermal hyperalgesia with a MED of 30 mg/kg (FIG. 1b). The highest dose of 30 mg/kg gabapentin prevented the hyperalgesic response for 24 hours (FIG. 1b). Similar administration of S-(+)-3-isobutylgaba also dose-dependently (3–30 mg/kg, s.c.) prevented development of thermal hyperalgesia with a MED of 3 mg/kg (FIG. 1c). The 30 mg/kg dose of S-(+)-3-isobutylgaba was effective up to 3 days (FIG. 1c). The administration of morphine 0.5 hour before surgery dose-dependently (1–6 mg/kg, s.c.) antagonized the development of thermal hyperalgesia with a MED of 1 mg/kg (FIG. 1a). This effect was maintained for 24 hours (FIG. 1a).

Effects of Gabapentin, S-(+)-3-Isobutylgaba and Morphine Administered Before Surgery on Tactile Allodynia The effect of drugs on development of tactile allodynia was determined in the same animals used for thermal hyperalgesia above. One hour was allowed between thermal hyperalgesia and tactile allodynia tests. Gabapentin dose-dependently prevented development of tactile allodynia with a MED of 10 mg/kg. The 10 and 30 mg/kg doses of gabapentin were effective for 25 and 49 hours, respectively (FIG. 2b). S-(+)-3-Isobutylgaba also dose-dependently (3–30 mg/kg) blocked development of the allodynia response with a MED of 10 mg/kg (FIG. 2c). This blockade of the nociceptive response was maintained for 3 days by the 30 mg/kg dose of S-(+)-3-isobutylgaba (FIG. 2c.). In contrast, morphine (1–6 mg/kg) only prevented the development of tactile allodynia for 3 hour postsurgery at the highest dose of 6 mg/kg (FIG. 2a).

Effect of S-(+)-3-Isobutylgaba Administered 1 Hour After Surgery on Tactile Allodynia and Thermal Hyperalgesia The allodynia and hyperalgesia peaked within 1 hour in all animals and was maintained for the following 5 to 6 hours. The s.c. administration of 30 mg/kg S-(+)-3-isobutylgaba 1 hour after surgery blocked the maintenance of tactile allodynia and thermal hyperalgesia for 3 to 4 hours. After this time, both nociceptive responses returned to control levels indicating disappearance of antihyperalgesic and antiallodynic actions (FIG. 3).

Gabapentin and S-(+)-3-isobutylgaba did not affect PWL in the thermal hyperalgesia test or tactile allodynia scores in the contralateral paw up to the highest dose tested in any of the experiments. In contrast, morphine (6 mg, s.c.) increased PWL of the contralateral paw in the thermal hyperalgesia test (data not shown).

The results presented here show that incision of the rat plantaris muscle induces thermal hyperalgesia and tactile allodynia lasting at least 3 days. The major findings of the present study are that gabapentin and S-(+)-3-isobutylgaba are equally effective at blocking both nociceptive responses. In contrast, morphine was found to be more effective against thermal hyperalgesia than tactile allodynia. Furthermore, S-(+)-3-isobutylgaba completely blocked induction and maintenance of allodynia and hyperalgesia.

What is claimed is:

1. A method for treating pain comprising administering a therapeutically effective amount of a compound of Formula I

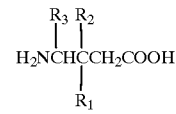

or a pharmaceutically acceptable salt, diastereomer, or enantiomer thereof wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl to a mammal in need of said treatment.

2. A method according to claim 1 wherein the compound administered is a compound of Formula I wherein $R_3$ and $R_2$ are hydrogen, and $R_1$ is —$(CH_2)_{0-2}$—i $C_4H_9$ as an (R), (S), or (R,S) isomer.

3. A method according to claim 1 wherein the compound administered is named (S)-3-(aminomethyl)-5-methylhexanoic acid and 3-aminomethyl-5-methyl-hexanoic acid.

4. A method according to claim 1 wherein the pain treated is inflammatory pain.

5. A method according to claim 1 wherein the pain treated is neuropathic pain.

6. A method according to claim 1 wherein the pain treated is cancer pain.

7. A method according to claim 1 wherein the pain treated is postoperative pain.

8. A method according to claim 1 wherein the pain treated is phantom limit pain.

9. A method according to claim 1 wherein the pain treated is bum pain.

10. A method according to claim 1 wherein the pain treated is gout pain.

11. A method according to claim 1 wherein the pain treated is osteoarthritic pain.

12. A method according to claim 1 wherein the pain treated is trigeminal neuralgia pain.

13. A method according to claim 1 wherein the pain treated is acute herpetic and postherpetic pain.

14. A method according to claim 1 wherein the pain treated is causalgia pain.

15. A method according to claim 1 wherein the pain treated is idiopathic pain.

* * * * *